United States Patent [19]

Dinelli

[11] 4,255,989
[45] Mar. 17, 1981

[54] CONVERTING ROTARY MOTION INTO VARIABLE-AMPLITUDE RECIPROCATION

[76] Inventor: Dino Dinelli, Via Miralago 3 - Albano Laziale, Rome, Italy

[21] Appl. No.: 972,344

[22] Filed: Dec. 22, 1978

[30] Foreign Application Priority Data

Jan. 6, 1978 [IT] Italy .............................. 19057 A/78
May 12, 1978 [IT] Italy .............................. 23335 A/78

[51] Int. Cl.³ ...................... F16H 35/08; F01B 31/14
[52] U.S. Cl. ........................................ 74/831; 74/44; 92/13.7
[58] Field of Search .................. 74/828, 831, 832, 41, 74/44, 45, 51; 92/13, 13.7

[56] References Cited

U.S. PATENT DOCUMENTS

| 2,806,431 | 9/1957 | Woydt ............................... 92/13.7 X |
| 3,103,173 | 9/1963 | Griswold .......................... 92/13.7 X |
| 3,162,131 | 12/1964 | Clark ............................... 92/13.7 X |

FOREIGN PATENT DOCUMENTS

| 914283 | 6/1946 | France ....................... 92/13.7 |
| 450347 | 7/1936 | United Kingdom ............ 92/13.7 |

*Primary Examiner*—Lawrence J. Staab
*Attorney, Agent, or Firm*—Morgan, Finnegan, Pine, Foley & Lee

[57] ABSTRACT

For transferring a rotary drive to a movable member in order that the latter may be reciprocated with a variable amplitude stroke, a mechanism is disclosed which comprises two parallel shafts, each carrying an arm or a disc; a peripheral pin on each disc being pivoted to one end of a connecting rod, the opposite end of which is pivoted to the either end of a rocker. The central pivot of the rocker is borne by a member which is so guided that only a reciprocal motion is permitted thereto.

8 Claims, 3 Drawing Figures

CONVERTING ROTARY MOTION INTO VARIABLE-AMPLITUDE RECIPROCATION

This invention relates to a mechanism for transferring the drive from a rotary shaft to a movable member to be reciprocated with a variable-amplitude stroke.

The mechanism is characterized in that the variable-stroke rectilinear reciprocation of the movable member is produced by connecting such member with the center of a rocker, the latter having at its ends two pins equally spaced apart from said center, the pins being connected, in their turn, to two connecting rods which are actuated, respectively, by two eccentric pins placed on two discs or on two arms which rotate at the same frequency, and by varying the phase shift between the circular motions of the two eccentric pins.

The ratio of the maximum to the minimum amplitude of the reciprocation is a function of the ratios which are selected between the geometrical dimensions, such as the distance between the centers of rotation of the discs or the arms, the radii of rotation and other parameters; but, no matter how these are selected, it is virtually impossible to annul the minimum reciprocation amplitude.

Thus, the present application discloses also a particular configuration of the system which permits to annul the minimum amplitude of the reciprocal motion.

Such a result is made possible when each of the two connecting rods which connect the pins of the rotary arms or discs with the pins placed at the rocker ends, is replaced by three connecting rods connected to each other, the central one of which is bound to a rectilinear motion along the axis passing through the center of rotation of the rotary arm or disc to which said central connecting rod is connected.

Obviously, the desired result of annulling the amplitude of the reciprocation when the phase shift between the two rotary discs or arms is 0 degrees (if the directions of rotation are contrary to one another), or 180 degrees (if the directions of rotation are concordant) can be obtained only by selecting the geometrical dimensions of the system properly (radius of rotation of the pins of the rotary discs or arms, distance between the two centers of rotation of such discs or arms, length of the connecting rods, length of the rocker and others).

Another feature of the invention is that the rotary shaft intended to transfer the drive to the movable member is bound to the motion of either rotary disc or arm whereas the other rotary disc or arm is bound to a second rotary shaft, the latter shaft being actuated by the former shaft by a gearing contained in a differential gear box, and the phase shift between the circular motions of the two discs or arms can be varied at will from 0° to 180° by properly rotating the gearbox which contains the differential gearing.

The mechanism of this invention can be used with satisfactory efficiency even when the driving powers to be transferred are comparatively high.

It is known that the conversion of a rotary motion into a reciprocation, whenever a high power drive is to be transferred, is usually provided by connecting via a connecting rod an eccentrical pin, placed on a rotary disc or an arm, with the head of a movable rod the motion of which is bound to a rectilinear path. The amplitude of the reciprocation stroke obtained with such a mechanism is fixed and is about twice the eccentricity. A variation of the amplitude of the reciprocation can only be obtained by varying the value of the eccentricity of the pin, that is to say, by replacing the rotary disc (or arm) by another disc (or arm) wherein the eccentricity of the pin is different. Such an operation is obviously feasible only when the machine is at standstill.

It would be also possible to operate by using a disc (or an arm) equipped with a slidable pin, i.e. a pin that can be brought either toward, or away of, the center of rotation, and, with appropriate devices, it is possible to carry out such shifts even during the operation of the machine. However, when the powers transferred are high, the use of movable pins does not prove satisfactory.

Other further approaches suggested and embodied heretofore, such as for example that which is based on the use of a swash plate having a variable obliquity relative to the axis of rotation, did not solve the problem, in actual practice, when the drives to be transferred are comparatively high.

The mechanism of the instant invention can better be illustrated with reference to the accompanying drawings, wherein.

Figure 1:
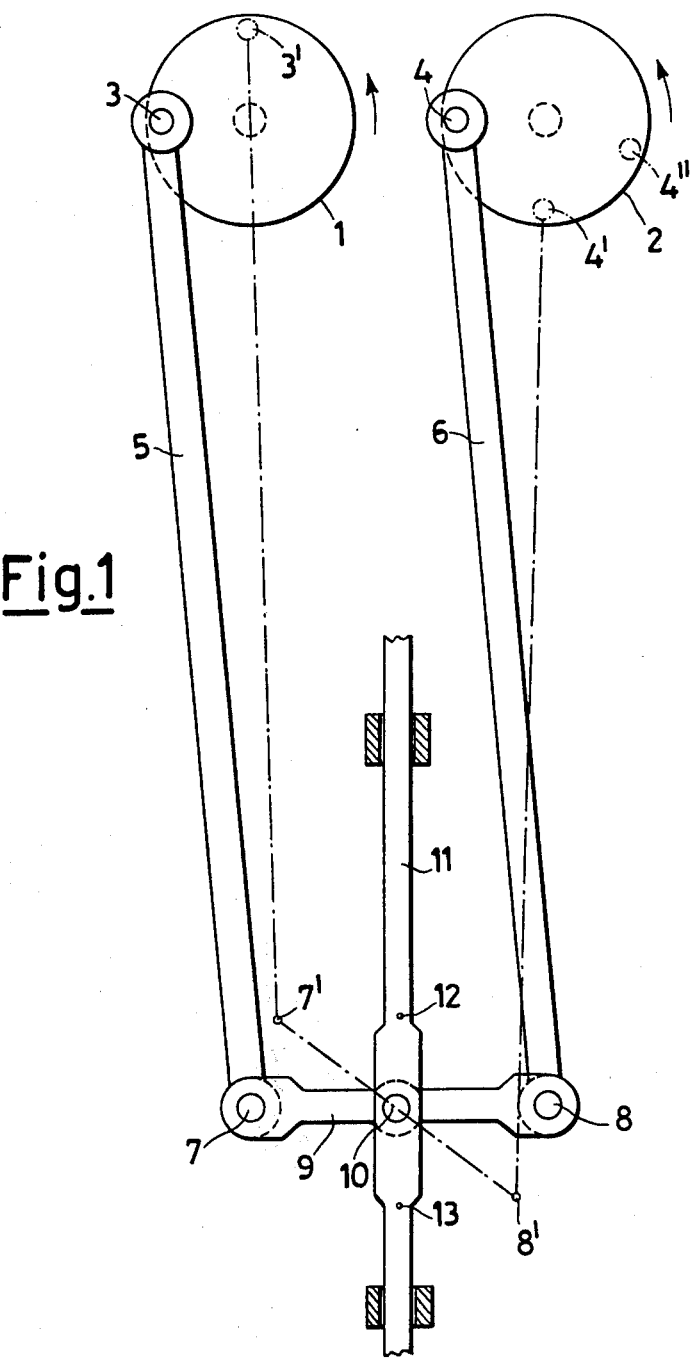
FIG. 1 shows an embodiment of the linkage assembly.

In FIG. 1, the two discs, 1 and 2, rotated at the same frequency and fitted with two pins, 3 and 4, placed equally spaced apart from the relative centers of rotation, are connected by means of the connecting rods 5 and 6 of the pins 3 and 4, with the pins 7 and 8 which are placed at the ends of the rocker 9. The latter, is connected by means of the central pin 10 to the rod 11, which can be moved only reciprocably. If the two discs 1 and 2 are rotated concordantly and are phase-concordant as in FIG. 1, the pins 3 and 4 are rotated while maintaining constantly homothetic positions, and the pin 10 (and the rod 11 therewith) is reciprocated between the points 12 and 13.

If the direction of rotation of the disc 1 is reverse relative to that shown in FIG. 1, after a quarter of revolution, the pins 3 and 4 are in the positions 3' and 4', whereas the pins 7 and 8 of the rocker 9 are at 7' and 8', respectively, and the position of 10 remains virtually unmodified. Stated another way, as the discs are rotated, the rocker oscillates whereas the pin 10 remains virtually stationary so that the amplitude of the reciprocation of 11 is nearly zero or so.

Similar, but opposite, results would be achieved if the initial position of the pin 4 were at 4''. In this case, the rocker would swing if the discs should rotate in the same direction, while the pin 10 is reciprocated between 12 and 13 if the discs are rotated in directions opposite to one another.

Of course, for phase shifts between 0° and 180°, such as those of the examples discussed above, the pin 10 with the rod 11 is reciprocated with intermediate amplitudes.

As can be seen, irrespective of the direction of rotation of each of the two discs, it is always possible to vary in a continuous way the amplitude of reciprocation of the rod 11 by varying the phase shift between the two rotary discs. The minimum and the maximum amplitude of the reciprocation is a function of the ratios between a few geometrical parameters, viz. the distance between the centers of rotation, the radii of the discs, the lengths of the connecting rods 5 and 6 and the length of the rocker 9. The ratios shown in FIG. 1 are anyhow sufficient to have amplitudes variable between a negligible magnitude and a value very near to the diameter of the circular paths of 3 and 4.

Figure 2:
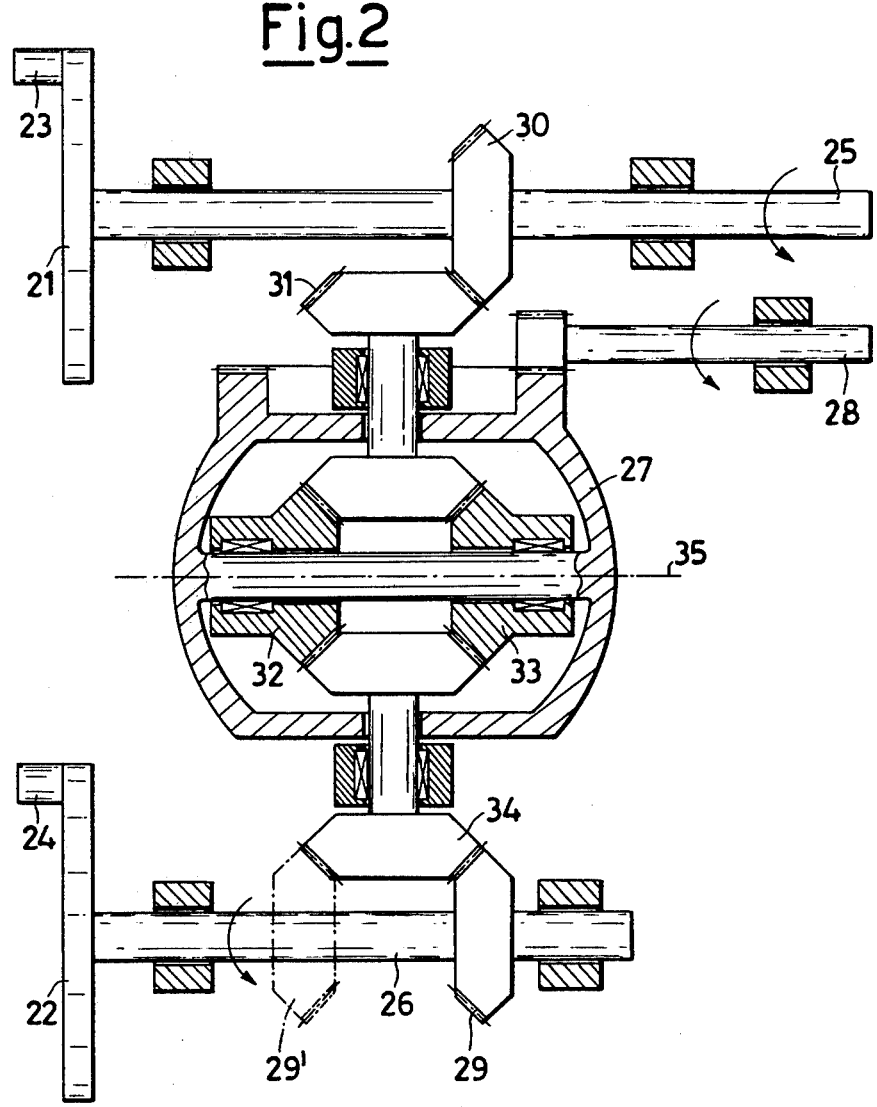
FIG. 2 shows the mechanism for varying the phase shift between the rotary discs.

In FIG. 2 there is shown the device by means of which it becomes possible to vary at will the phase shift between the two rotary discs while these are being rotated.

The driving shaft 25, which is rotated by the drive source, actuates directly the rotary disc (or arm) 21 fitted with the pin 23.

The shaft 25 transfers its drive also to the rotary shaft 26 by means of a differential gearbox 27.

The shaft 26 rotates the disc 22 fitted with the pin 24.

The shaft 28 can, at will, latch or rotate the differential box. If the initial position is that shown in FIG. 2 and the shaft 25 begins to be rotated in the direction shown, if 28 is blocked, and thus the differential box is held stationary, the rotation of 25 is transferred also to 26 and the discs 21 and 22 are driven to rotation with the same frequency in the same direction (should it be desired to reverse the rotation of 22, it suffices to switch the pinion 29 to the position 29' shown in dotted lines). The pins 23 and 24 are phase-concordant so that the amplitude of the reciprocation is at its top value.

Let us now consider again the initial position with the shaft 25 at standstill. Let it be assumed that the shaft 28 is rotated in the direction of the arrow so that the differential box 27 is rotated through 90 degrees so that the axis 35 is placed in a position perpendicular to the plane of the sheet of the drawing. During the motion of the differential box, the pinion 31 remains stationary since 25 is stationary, the pinions 32 and 33 go through a quarter of a revolution in the contrary direction so that 34 is rotated by a half-circle and rotates the shaft 26 and the disc 22, and the result is that the pin 24 is shifted by 180 degrees. Between the two pins 23 and 24, there has thus been provided a phase shift as wide as 180°. Then by properly rotating the shaft 28 it becomes possible to establish a phase shift at will between the pins 23 and 24.

This is valid also for the mechanism when in operation. As a matter of fact, if the axle 25 is rotated at a certain speed and 28 is stationary, the pinions 30, 31, 34 and 29 are likewise rotated at the same speed. By rotating 28 and thus the differential box 27 while 30 and 31 maintain their motion since the latter is bound to the motion of the shaft 25, the pinions 32, 33 and 34 undergo an additional motion which is added to the existing motion until 28 remains in rotation. When the rotation of 28 is discontinued, the pinion 34 is restored to the rate of revolution of the pinion 31 but it retains the phase shift which took place during the motion of 28. The diagram shown in FIG. 2, of course, can undergo changes such as for example the arrangement of the shafts 25 and 26 in directions perpendicular to one another, the replacement of the discs 21 and 22 by crankshaft, the production of the rotation of the differential box by the agency of the lever and otherwise, without departing from the scope of this invention, which is defined by the connection between the rotary motions of 25 and 31, and by the connection of the rotary motions of 25 and 26 through the differential gear assembly.

The mechanism sharply differs from those using differential boxes (such as in motor vehicles) because the power is transferred to the shaft 25 (and thus to the pinion 31), rather than to the shaft 28 which transfers the drive to 31 and to 34 through the rotation of the differential box.

The mechanism according to the present invention is composed by well known component parts which are usually manufactured in several types and sizes for various uses.

This circumstance affords the opportunity of economy of construction and the reliability of operation even for long service periods of machines based on the mechanism of this invention.

On the other hand, the manner in which the component parts are associated together and employed is entirely novel and accounts for the novelty and the ingenuity of the invention.

Figure 3:
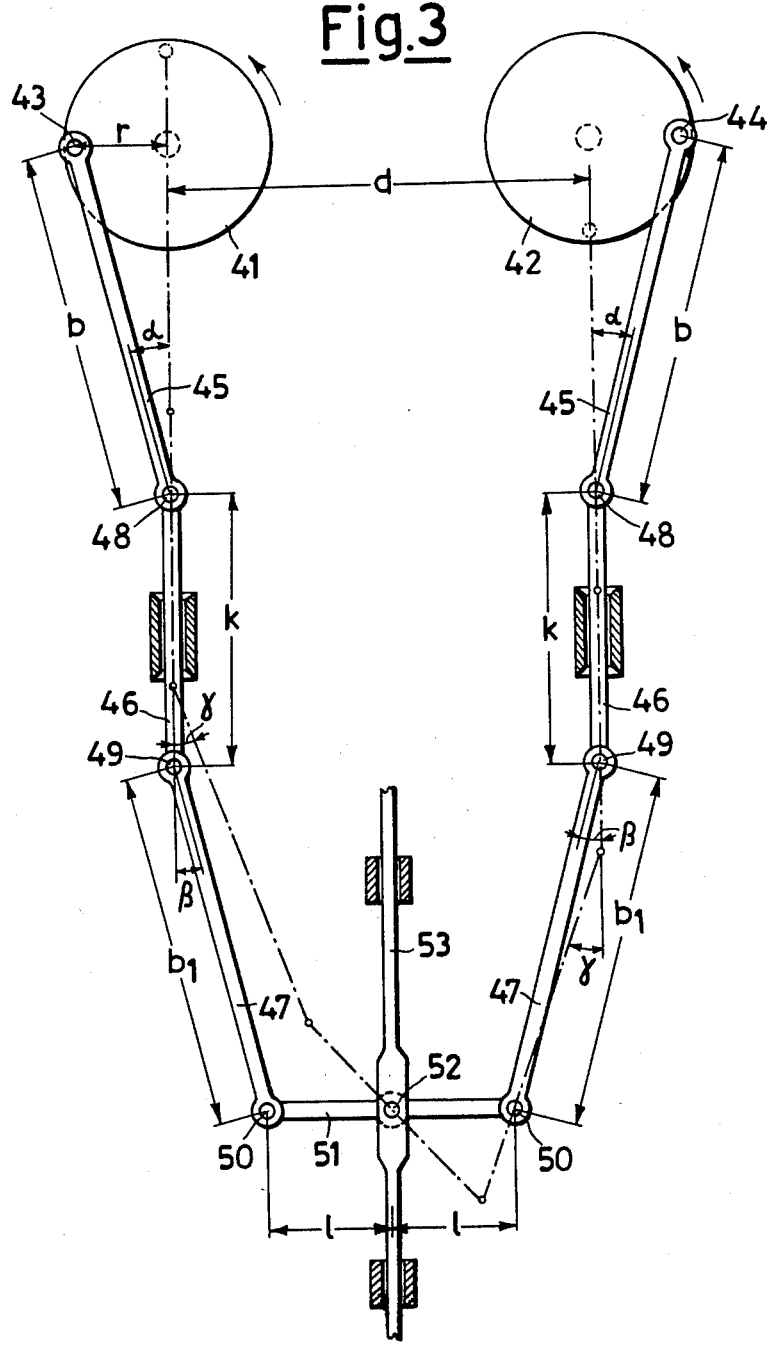
FIG. 3 shows a particular configuration of the system by which the minimum amplitude of the reciprocation can be annulled.

FIG. 3 relates to a particular configuration of the mechanism which affords an opportunity to annual the minimum amplitude of the reciprocal motion.

In FIG. 3, the two discs 41 and 42 which are rotated at the same frequency and are fitted with the pins 43 and 44 placed equally spaced apart from the centers of rotation, are connected, by means of the connecting rods 45, 46, 47 and the pins 48, 49, 50, with the ends of the rocker 51 which, by means of the central pin 52 is connected to the rod 53 which is movable only reciprocably.

In the same FIGURE, b indicates the length of the connecting rods 45, K is the length of the connecting rods 46, $b_1$ is the length of the connecting rods 47, l is the radius of the oscillation of the rocker 51, r is the radius of rotation of the pins 43 and 44, d is the distance between the two centers of rotation of the pins 43 and 44, alpha and Beta are the angles formed by the connecting rods 45 and 47 with the vertical when the pins 43 and 44 are on the horizontal line passing through the centers of rotation of the same pins, $\gamma$ is the angle that the connecting rods 47 form with the vertical when the pins 43 and 44 are, respectively, the former in the top point and the latter in the bottom point of the circumference they travel along.

Of course, terms such as "top", "bottom", "vertical" and "horizontal" refer exclusively to FIG. 3, since the entire mechanism can be rotated at will without any change in the results.

It has been found that, in order that the minimum amplitude of the reciprocation may be annulled, the geometrical dimensions of the system should be so selected as to satisfy the relationship:

$$b \cos \alpha + b_1 \cos \beta = b + b_1 \cos \gamma$$

To find dimensional values which satisfy the zero condition reported above consistently with the requirements to be fulfilled is a simple mathematical calculation. For example, in FIG. 3 it has been assumed that a maximum amplitude of reciprocation of 4 was sought for.

By adopting, for example, the values
$b = b_1 = 8$
$r = 2$ (corresponding to the maximum stroke of 4)
$k = 6$
$d = 9.5$
$l = 3.75$, the result is that
$\alpha = \beta = 14°30'$
$\cos \alpha = \cos \beta = 0.9682$
$\gamma = 20°30'$
$\cos \gamma = 0.9367$
so that the zeroizing condition is fulfilled inasmuch as 8 by 0.9682+8 by 0.9682=15.49=8+8 by 0.9367.

Of course, in the case in which, by way of example, it has been emphasized the requirement of having a determined value (4) of the maximum amplitude, the solution which has been indicated is but one of the infinite possible solutions.

The possibility of reducing to zero the minimum amplitude of the reciprocation has a considerable importance for a number of practical applications, such as when the mechanism is to be applied to actuating a reciprocating pump which introduces a liquid into a pressurized system.

In such cases, in fact, the resistance force remains constant irrespective of the reciprocation amplitude, even if very slight, but not zero.

The start must thus take place with the motive source under load so that the necessity of special device becomes imperative.

When, conversely, it becomes possible to annul the pump stroke completely, start can be obtained even if no work is accomplished and the motor can be started virtually without effort; it is thus possible to put the motor under load gradually only when it has attained a certain number of revolutions of steady run. A wide field of application of the mechanism of the invention can be found in its connection with variable-stroke reciprocating pumps.

As mere nonlimiting examples in this connection, there can be cited:

(a) the movement of liquids in continuous processes in which variations of the rate of flow in operation are desirable, (b) the integral exploitation of widely variable motive powers such as those of the wind motors for pumping liquids, and (c) the optimum exploitation of a fixed available power, such as when, for example, it is required to pump through a long pipeline liquids of variable properties (to which different pressure drops correspond) or when it is required to pump the same liquid to different levels, such as it occurs when a large reservoir is filled by pumping liquid upwards thereinto.

Of course, in the individual particular applications, the adjustment of the phase shift to bring the amplitude of the reciprocation to the most suitable magnitude can be made automatic by servoing the rotation of the differential box to the magnitudes of an appropriately selected measurable parameter.

I claim:

1. A mechanism for transferring the drive from a rotary shaft to a variable-stroke reciprocable member which provides for the variable-amplitude reciprocation of the movable member while annulling the minimal amplitude thereof, comprising:

two discs or arms which are rotated at the same frequency;

a pin on each disc or arm equally spaced apart from the centers thereof;

two sets of three connecting rods connected pairwise by pivotal pins wherein one of the outer rods of each set is connected to one of said pins on said disc or arm, and wherein the intermediate connecting rod of each set is positioned so as to be bound to a reciprical motion along the vertical axis passing through the center of rotation of said disc or arm;

a rocker having ends which are pivotally connected by pins to the other of said outer rods of said rod sets and a center which is connected by a pin to the variable-stroke reciprocable member, and wherein the geometrical dimensions of the mechanism are selected in accordance with the following relationship to annul the minimal amplitude:

$$b \cos \alpha + b_1 \cos \beta = b + b_1 \cos \gamma$$

wherein b is the length of said connecting rods which unite said pins of said rotary discs or arms with said intermediate connecting rods, $b_1$ is the length of said connecting rods which unite said intermediate connecting rods with said pins of said rocker, $\alpha$ is the angle formed by said connecting rods having the length b with the vertical when said pins of said rotary discs or arms lie on the horizontal line passing through the centers of rotation, $\beta$ is the angle formed by said connecting rods having the length $b_1$ with the vertical when said pins of the rotary discs or arms lie on the horizontal line passing through the centers of rotation, $\gamma$ is the angle formed by said connecting rods having the length $b_1$ with the vertical when said pins of the rotary discs or arms are with one on the top point and with the other on the bottom point of their circular path.

2. A mechanism according to claim 1, characterized in that it is adapted to vary the amplitude of the reciprocation from between zero to a preselected value by varying at least one of the following: the phase shift and the direction of rotation between the circular motions of said two pins placed on said two discs or arms.

3. A mechanism according to claim 1, wherein the rotary shaft intended to transfer the drive to the reciprocable member of variable amplitude is bound to the motion of one of said rotary discs or arms and the other of said discs or arms is bound to a second rotary shaft actuated by the first shaft by a set of gears held in a differential box.

4. A mechanism according to claim 3, wherein the phase shift between the rotary motions of the two discs or arms can be varied at will from 0° to 180° by causing the differential box to be rotated.

5. A mechanism according to claim 3, characterized in that under stationary conditions of operation the differential box is not rotated and the phase shift between the two rotary shafts remains a constant.

6. A mechanism according to claim 3, characterized in that the two rotary discs or arms are rotated in the same direction.

7. A mechanism according to claim 3, characterized in that the two rotary discs or arms are rotated in directions contrary to one another.

8. A mechanism according to the preceding claim 1, wherein the variable-amplitude reciprocable member is adapted to be connected to a reciprocating pump so as to obtain the regulation of the rate of delivery of the pump even during the operation.

* * * * *